US00PP14382P39

(12) United States Plant Patent
Pieters

(10) Patent No.: US PP14,382 P3
(45) Date of Patent: Dec. 16, 2003

(54) CHRYSANTHEMUM PLANT NAMED 'GEDI TWO OMOL'

(50) Latin Name: *Chrysanthemum morifolium*
Varietal Denomination: Gedi Two Omol

(75) Inventor: Dirk Pieters, Staden (BE)

(73) Assignee: Pieters Plant Production, BVBA, Oostniewkerke (BE)

( * ) Notice: Subject to any disclaimer, the term of this patent is extended or adjusted under 35 U.S.C. 154(b) by 0 days.

(21) Appl. No.: 10/137,810

(22) Filed: May 1, 2002

(65) Prior Publication Data

US 2003/0208815 P1 Nov. 6, 2003

(51) Int. Cl.[7] ..... A01H 5/00

(52) U.S. Cl. ..... Plt./290

(58) Field of Search ..... Plt./287, 290, 289

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 42 days of short day length, free branching habit, dark orange ray florets at first opening, with outer ray florets fading to a lighter orange and the center remaining dark at maturity and all ray florets changing to lighter orange with fading, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Omol.'

BACKGROUND OF THE INVENTION

The new cultivar is a product of a naturally occurring mutation discovered in a cultivated state on a branch of a Chrysanthemum plant variety 'Molfetta Pink' (undistributed in the United States). The new cultivar was discovered and selected by the inventor in September 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Omol' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Omol.' These characteristics in combination distinguish 'Gedi Two Omol' as a new and distinct Chrysanthemum cultivar:

1. Decorative-type inflorescence,
2. Consistent flowering response to short days, blooming consistently after 42 days of short day length,
3. Free branching habit, 4. Dark orange ray florets at first opening, with outer ray florets fading to a lighter orange and the center remaining dark at maturity and all ray florets changing to lighter orange with fading,
5. Very uniform round growth habit, and
6. Large quantity of blooms per flowering branch.

Plants of the new cultivar are similar to plants of the parent variety, 'Molfetta Pink' in most horticultural characteristics, however plants of the new cultivar have ray florets of a different color and inflorescences of a smaller diameter than plants of the parent variety.

In comparison to the commercially available variety 'Gedi One Nov' (U.S. Plant Pat. No. 13,796), 'Gedi Two Omol' has fewer florets per inflorescence, fewer disc florets per inflorescence, a shorter blooming response time to short days, and a smaller diameter inflorescence.

BRIEF DESCRIPTION OF THE PHOTOGRAPH

The photograph shows a plant of 'Gedi Two Omol' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 96 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Omol'.

Commercial classification: Garden-type Chrysanthemum.

Parentage: Naturally occurring mutation on one branch of the parent variety 'Molfetta Pink'.

PROPAGATION

Time to rooting: 7 to 14 days at approximately 21° C.
Root description: Fine; fibrous.

PLANT

Growth habit: Mounding herbaceous perennial.
Height: Approximately 25 cm.
Spread: Approximately 26.5 cm.
Growth rate: Moderate.
Branching characteristics: Free Branching.
Length of lateral branches: Approximately 23.3 cm.
Number of leaves per lateral branch: Approximately 13.

FOLIAGE

Leaf:
- *Arrangement.*—Alternate.
- *Average length.*—Approximately 5 cm.
- *Average width.*—Approximately 4.1 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—young foliage upper side: Near 137A. young foliage under side: Near 138A. mature foliage upper side: Near 139A. mature foliage under side: Near 138A. venation upper side: Near 138C. venation under side: Near 138B.
- *Venation type.*—Palmately net.

Petiole:
- *Average length.*—Approximately 3.2 cm.
- *Color.*—Near 139A.
- *Diameter.*—Approximately 0.3 cm.

BLOOM

Inflorescence:
- *Flowering habit.*—Induced by darkness period greater than 13.5 hours, approximately 42 days of appropriate day length required to induce and develop blooms.
- *Inflorescence form.*—Decorative.
- *Natural flowering season.*—Approximately the first two weeks of September.
- *Number of inflorescences per lateral branch.*—Approximately 15.
- *Inflorescence diameter.*—Approximately 2.5 cm.
- *Inflorescence depth.*—Approximately 1.2 cm.
- *Inflorescence longevity on plant.*—Approximately 26 days.
- *Persistence.*—Persistent.

Ray florets:
- *Appearance.*—Matte.
- *Texture.*—Smooth.
- *Average number per flower.*—186.
- *Shape.*—Obovate.
- *Aspect.*—Flat.
- *Margin.*—Approximately one-half of ray florets—entire, Approximately one-half of ray florets —deeply lobed with one or two lobes.
- *Apex.*—Fringed.
- *Length.*—Approximately 1.1 cm.
- *Width.*—Approximately 0.5 cm.
- *Color.*—upper surface at first opening: Near 167A. upper surface at maturity: Near 23B. upper surface at fading: Near 20A. under surface at first opening: Near 173D. under surface at maturity: Near 22D. under surface at fading: Near 20C.

Disc florets:
- *Appearance.*—Shiny.
- *Texture.*—Smooth.
- *Average number per flower.*—Approximately 3.
- *Shape.*—Cylindric.
- *Apex.*—Obtuse.
- *Average length.*—Approximately 0.3 cm.
- *Average width.*—Approximately 0.1 cm.
- *Color.*—at first opening: Near 13B. at maturity: Near 13A. at fading: Near 13A.

Peduncle:
- *Length.*—at terminal end (shortest): Approximately 3 cm. at lateral end (longest): Approximately 6 cm.
- *Angle to stem.*—Acute.
- *Strength.*—Moderate.
- *Color.*—Near 138B.
- *Habit.*—Upright.
- *Diameter.*—Approximately 0.1 cm.
- *Surface texture.*—Lightly pubescent.

Inflorescence bud:
- *Length.*—Approximately 0.4 cm.
- *Diameter.*—Approximately 0.7 cm.
- *Form.*—Globular.
- *Color.*—Near 139C.

Involucral bracts (phyllaries):
- *Appearance.*—Matte.
- *Texture.*—Lightly pubescent.
- *Number.*—Approximately 27.
- *Shape.*—Oblanceolate.
- *Margin.*—Entire.
- *Apex.*—Acute.
- *Length.*—Approximately 0.6 cm.
- *Width.*—Approximately 0.2 cm.
- *Color.*—upper side: Near 139C. under side: Near 139C.

REPRODUCTIVE ORGANS

Ray florets:
- *Number of pistils per flower.*—1.
- *Stigma shape.*—2 branched.
- *Stigma color.*—Near 3A.
- *Style color.*—Near 154B.
- *Style length.*—Approximately 0.4 cm.
- *Stamens.*—Absent.

Disc florets:
- *Number of pistils per flower.*—1.
- *Stigma shape.*—Two-branched.
- *Stigma color.*—Near 13B.
- *Style length.*—Approximately 0.3 cm.
- *Style color.*—Near 154D.
- *Number of stamens per flower.*—5.
- *Anther shape.*—Tubular.
- *Anther color.*—Near 13A.
- *Pollen.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Omol' as herein illustrated and described.

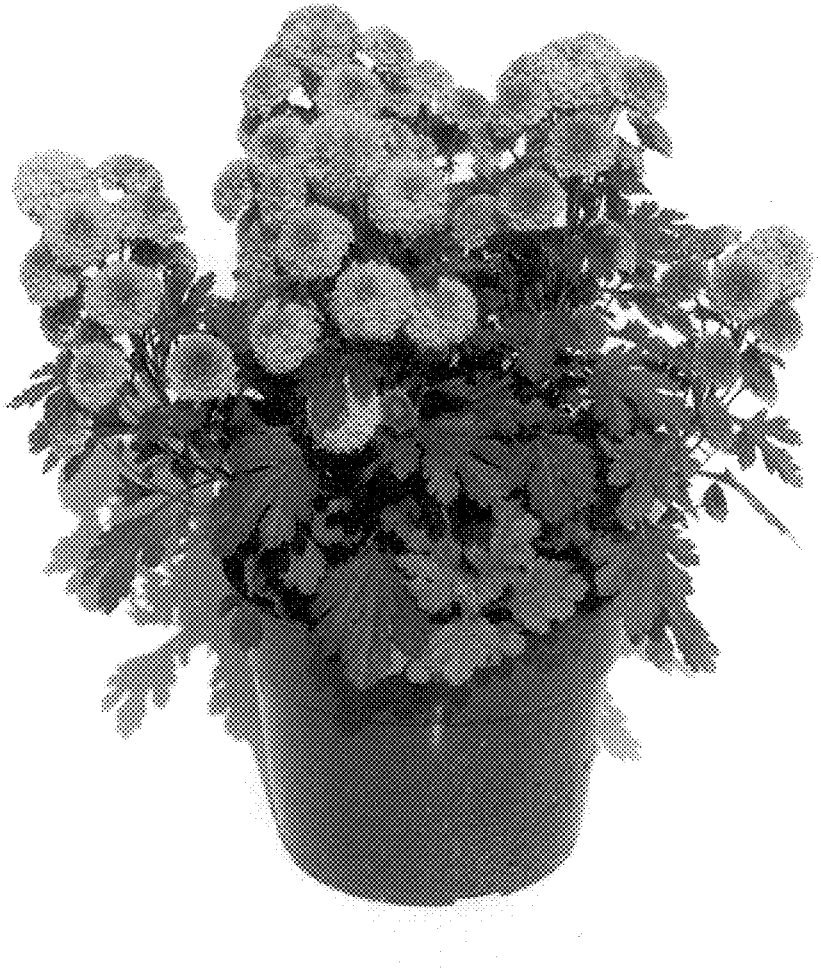

* * * * *